US008794965B2

(12) United States Patent
Latiolais

(10) Patent No.: US 8,794,965 B2
(45) Date of Patent: Aug. 5, 2014

(54) METHODS AND APPARATUSES FOR RESTORING AND IN-OFFICE CUSTOMIZING OF DENTAL IMPLANT ABUTMENTS WITH A DENTAL PROSTHESIS

(76) Inventor: Lon Jude Latiolais, Georgetown, TX (US)

(*) Notice: Subject to any disclaimer, the term of this patent is extended or adjusted under 35 U.S.C. 154(b) by 630 days.

(21) Appl. No.: 12/660,306

(22) Filed: Feb. 24, 2010

(65) Prior Publication Data

US 2011/0207082 A1 Aug. 25, 2011

(51) Int. Cl.
*A61C 8/00* (2006.01)
(52) U.S. Cl.
USPC .......................................................... 433/173
(58) Field of Classification Search
USPC ................................ 433/201.1, 215, 223, 143
See application file for complete search history.

(56) References Cited

U.S. PATENT DOCUMENTS

| 5,658,147 | A | * | 8/1997 | Phimmasone | 433/213 |
| 5,718,583 | A | * | 2/1998 | Flanagan | 433/141 |
| 5,718,586 | A | * | 2/1998 | Sharp et al. | 433/214 |
| 5,927,979 | A | * | 7/1999 | Misch et al. | 433/173 |
| 6,045,361 | A | * | 4/2000 | Misch et al. | 433/214 |
| 6,068,480 | A | * | 5/2000 | Misch et al. | 433/173 |
| 6,083,004 | A | * | 7/2000 | Misch et al. | 433/173 |
| 2005/0118552 | A1 | * | 6/2005 | Coopersmith | 433/136 |

OTHER PUBLICATIONS

"Closed and Open Tray Impressions"—by Zimmer Dental Inc.—Rev Jun. 2007—http://www.zimmerdental.com/pdf/lib_gdTsvopenAndClosedImpres4917.pdf.*
"Restorative Manual "Cast-To" Gold Abutment System"—by Zimmer Dental Inc.—Posted in the Internet Mar. 22, 2006—www.zimmerdental.com/pdf/lib_guidTsvAdvRestMan5of11.pdf.*
WaybackMachine date for "Restorative Manual "Cast-To" Gold Abutment System" e-document of Zimmer Dental Inc.*
"Simple Solution Prosthetic Technique Manual" by BioHorizons—Rev B Mar. 2008—http://www.biohorizons.com/documents/ML0142.pdf.*
WaybackMachine date for "Close and Open Tray Impression" e-document of Zimmer Dental Inc.*

* cited by examiner

*Primary Examiner* — Cris L Rodriguez
*Assistant Examiner* — Mirayda A Aponte

(57) ABSTRACT

Methods for providing a dental prosthesis to a mouth or to prepare a mouth for receiving a dental prosthesis include obtaining an impression of an installed implant abutment and the surrounding portion of a mouth. The implant abutment is then removed from the mouth, installed in an additional fixture, and placed in a corresponding region of the impression. The impression is placed over a cavity of a transfer member containing mold material such that the mold material acquires the shape of the impression, and the additional implant fixture is retained in the mold. Modifications can then be performed to the implant abutment within the mold, as the mold approximates the surrounding region of the mouth. The modified implant abutment can then be returned to the mouth, a final impression can be made and a crown, bridge or similar dental prosthesis can be fabricated.

14 Claims, 11 Drawing Sheets

METHODS AND APPARATUSES FOR RESTORING AND IN-OFFICE CUSTOMIZING OF DENTAL IMPLANT ABUTMENTS WITH A DENTAL PROSTHESIS

CROSS REFERENCE TO RELATED APPLICATIONS

The present application claims priority to the co-pending United States patent application having the application Ser. No. 12/589,728, filed Oct. 28, 2009, the entirety of which is incorporated herein by reference.

FIELD

The present invention relates, generally, to methods and apparatuses usable to provide a dental prosthesis to a mouth, such as through modification of a dental implant abutment and provision of a crown, bridge, or similar prosthesis to the abutment.

BACKGROUND

When a tooth is damaged, missing, lost, or must be extracted for health reasons, one option available to a patient is the replacement of the lost tooth with a dental prosthesis. While numerous types of dental prostheses are available, dental implants are a generally effective, functional, and cosmetically successful prosthetic apparatus usable to replace a single tooth or group of teeth, while only minimally impacting adjacent and/or uninvolved teeth within the mouth.

Conventional methods for providing a dental implant to a patient first require a surgical procedure to install an implant fixture into the patient's jawbone at the location of the tooth to be replaced. Typically, an implant fixture consists primarily of a titanium screw, which is threaded into a hole that has been drilled or otherwise provided into the jawbone. A two to six month healing period normally follows this procedure before any further steps are taken, to allow the patient's bone to osteointergrate to the titanium implant fixture. During this time, a healing abutment or similar cover can be affixed to the implant fixture. Loading of the implant fixture before sufficient healing has occurred can cause the fixture to move and/or fail, requiring the procedure to be repeated, or possibly preventing use of a dental implant entirely.

Following the healing period, the healing abutment is removed, and a standard implant abutment is installed, which is generally formed from titanium, zirconia, or another similar material. While the dimensions and shapes of implant abutments can vary between dental implant systems, implant abutments are generally available in a range of standard sizes, depending on the tooth to be replaced, and are generally frustro-conical in shape. Due to the fact that each patient's mouth is unique, a standard implant abutment is often unsuitable for accommodating a crown or similar dental prosthesis to replace the lost tooth until modified, such as through grinding and/or machining, to suit the patient's mouth. In addition, conventional methods include the manufacture of the customized dental prosthesis at an off-site laboratory, which requires the patient to endure a certain amount of pain and discomfort for a period of days to weeks, while requiring several visits to a dental office to obtain and ensure a proper fitting with the dental prosthesis.

The typical handling procedure(s) of a standard implant manufacturer, include the following: once the implant is fully osteointergrated, the cover screw is uncovered and exposed via incision or similar method, the cover screw is removed, the healing abutment is placed using a hex screwdriver, and the healing process is permitted to occur. After an adequate healing period has occurred, the healing abutment is removed using the hex screwdriver, and the implant pick-up transfer is attached to the implant. Next, one or more pins are tightened firmly and an impression is taken using a customized impression tray and an elastic impression material. The impression is transported to an off-site laboratory where laboratory technicians will attach the implant replica onto the implant pick-up or implant transfer, tighten the pins, and fabricate a working stone model with a removable gingival modeling material. Then, the laboratory technicians will select and attempt to fit the appropriate abutment on the stone model, using trial and error unless properly instructed by the dentist. Next, the laboratory technicians will mount the abutment with an implant replica in a grinding handle and modify the abutment. It is then recommended that the patient return to the dental office to evaluate the fit of the modified implant within the mouth. Once it has been determined that the implant abutment has been suitably modified to accommodate a crown or similar dental prosthesis, and that the fit is proper, the abutment is again sent back to the laboratory or similar facility, where the crown is fabricated, using the implant abutment and the mold of the patient's mouth to ensure proper fit, function, and cosmetic appearance of the crown. After this final restoration is fabricated by the laboratory, the crown or dental prosthesis is transported to the dental office, and an additional office visit is required for the permanent restoration to be cemented into the patient's mouth.

The entirety of the customization and fitting processes following the healing period can require multiple days, if not weeks, depending on the availability of laboratory resources, and will require numerous dental office visits for a patient, thus incurring significant expense in the form of laboratory costs, dental equipment and costs, and the time associated with the multiple required office visits.

A need exists for methods and apparatuses for providing a dental prosthesis to a patient that can be performed efficiently, on-site, enabling a patient to be provided with a crown or similar dental prosthesis in a single office visit, that can be adapted to any implant procedure and/or system, including those in which implant loading is permitted and accepted upon initial placement.

A need also exists for methods and apparatuses for providing a dental prosthesis to a patient that can be performed without requiring specialized laboratory facilities and the associated expenses.

A further need exists for methods and apparatuses that enable manual manipulation and customization of molds and implant abutments using equipment readily available on-site at a dental office.

The present invention meets these needs.

BRIEF DESCRIPTION OF THE DRAWINGS

In the detailed description of the embodiments of the invention presented below, reference is made to the accompanying drawings, in which.

The depicted embodiments of the invention are described below with reference to the listed Figures.

DETAILED DESCRIPTION OF THE EMBODIMENTS

Before explaining the disclosed embodiments of the invention in detail, it is to be understood that the present invention is not limited to the particular embodiments depicted or described, and that the invention can be practiced or carried out in various ways.

The present invention relates, generally, to methods and apparatuses useable to provide a dental prosthesis to a mouth and/or to prepare a mouth for receiving a dental prosthesis. An impression of an installed implant abutment and a surrounding portion of a patient's mouth can be obtained, and used to form a mold immediately thereafter through use of a transfer member.

Embodiments of the transfer member can include a cavity and/or well having a curvature complementary to that of gingival tissue within a mouth, and a depth sufficient to accept an implant fixture, with a handle disposed beneath the cavity for facilitating manual manipulation and modification of an implant abutment disposed within a mold within the cavity.

After obtaining the impression, the implant abutment can be removed from the patient's mouth, attached to an additional implant replica fixture, and placed in a corresponding location within the impression. The impression and/or the transfer member can then be provided with a mold material, and the impression can be placed over the transfer member such that the implant fixture protrudes into the mold material while mold material assumes the shape of the impression. The implant fixture and abutment are retained within the mold in a position corresponding to the position of the implant abutment within the mouth, such that modifications and/or customizations can be provided to the abutment external to the mouth to prepare the abutment for receipt of a crown, bridge or similar dental prosthesis.

Figure 1:
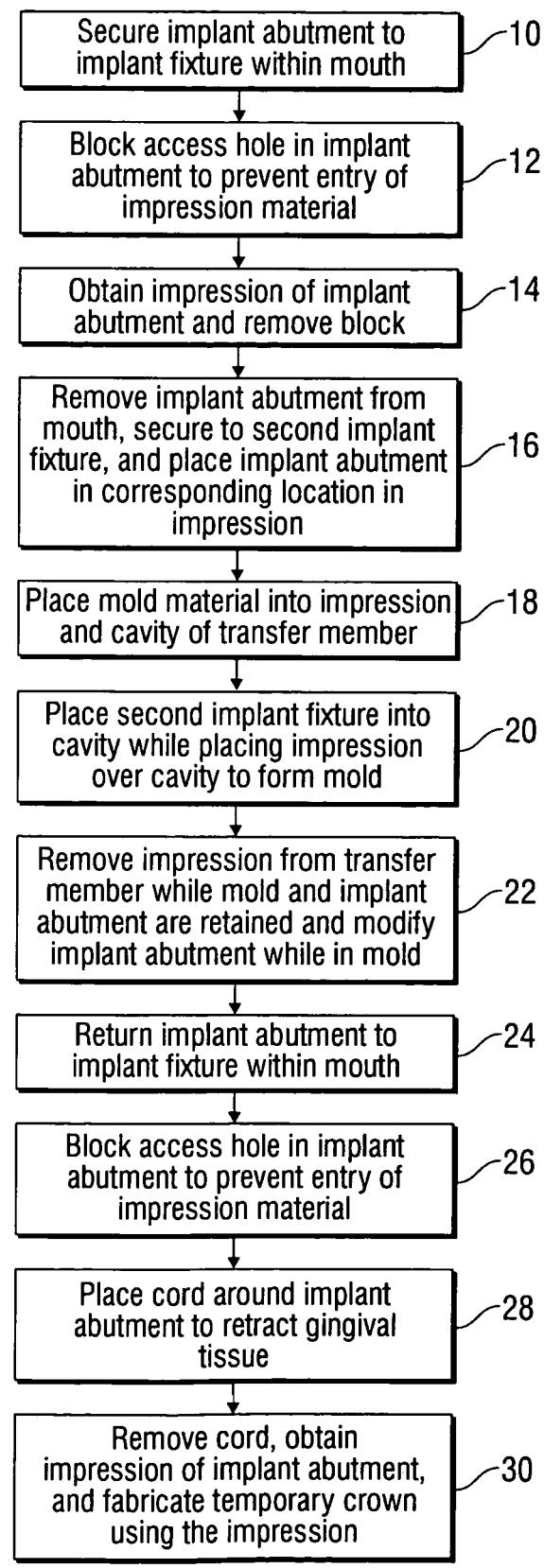
FIG. 1 is a diagram depicting an embodiment of the present method.

Referring now to FIG. 1, a diagram of an embodiment of a method for providing a mouth with a dental prosthesis is shown. Prior to the commencement of the depicted embodiment of the method, an implant fixture can be installed within a patient's mouth, and the passage of a sufficient period of time to permit healing can be permitted, as known in the art. An implant abutment can then be secured to the implant fixture within the mouth (10). Any manner of implant system is usable within the scope of the present invention. Generally, an implant abutment includes a titanium, frustro-conical member having an access hole therein, through which a threaded member, such as a hex screw, can be threaded to the implant fixture through use of a specialized tool to tighten the screw.

Figure 2:
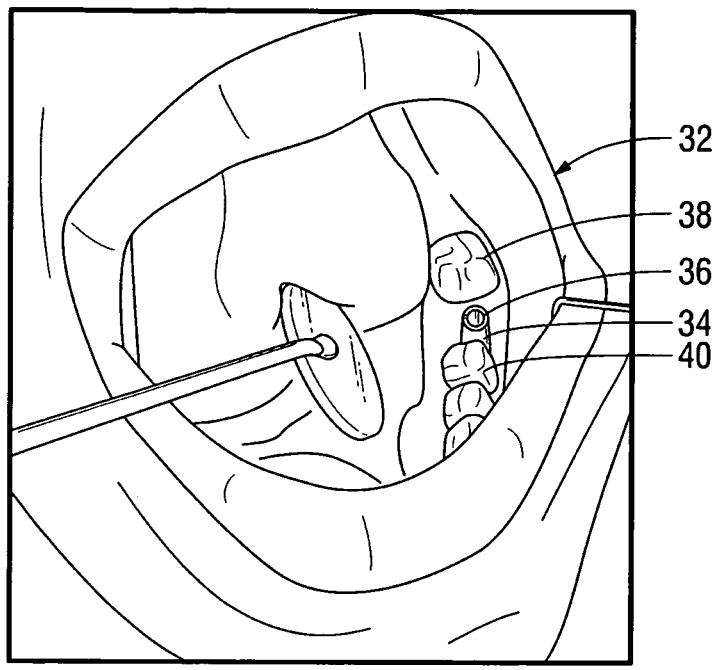
FIG. 2 depicts an implant abutment installed within a mouth.

FIG. 2 depicts an implant abutment (34) installed within a mouth (32) between a first adjacent tooth (38) and a second adjacent tooth (40). The depicted implant abutment (34) is shown as a generally frustro-conical member having an opening (36) disposed at its apex for receipt of a threaded member, such as a hex screw, usable to secure the implant abutment (34) to an implant fixture (not visible in FIG. 2) disposed beneath the gum line within the mouth (32). While FIG. 2 depicts an implant abutment (34) sized to replace a molar, it should be understood that implant abutments of any size or shape, to accommodate a prosthesis for any tooth, are usable within the scope of the present invention.

Returning to FIG. 1, after securing the implant abutment to the implant fixture within the mouth (10), an impression of the implant abutment and a surrounding portion of the mouth can be obtained (14). If the implant includes an access hole or similar opening, the access hole can be blocked (12) prior to obtaining the impression to prevent the entry of impression material into the implant abutment.

Figure 3:
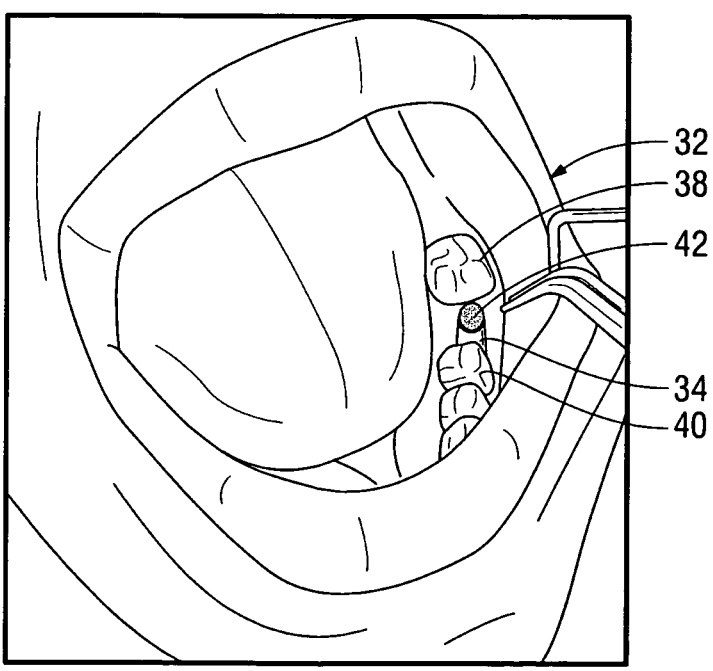
FIG. 3 depicts the implant abutment of FIG. 2 having an opening therein blocked to prevent entry of impression material into the implant abutment.

FIG. 3 depicts the implant abutment (34) of FIG. 2, disposed between adjacent teeth (38, 40) within the mouth (32). The opening (not visible in FIG. 3) disposed at the apex of the implant abutment (34) has been blocked using a plug (42), which is depicted as a piece of cotton. While compressible materials, such as cotton, are readily available and can be easily compressed for insertion into the access opening of an implant abutment, any generally solid material sized to fit within the access opening that is able to prevent the flow of impression material into the implant abutment can be used when necessary.

Figure 4:
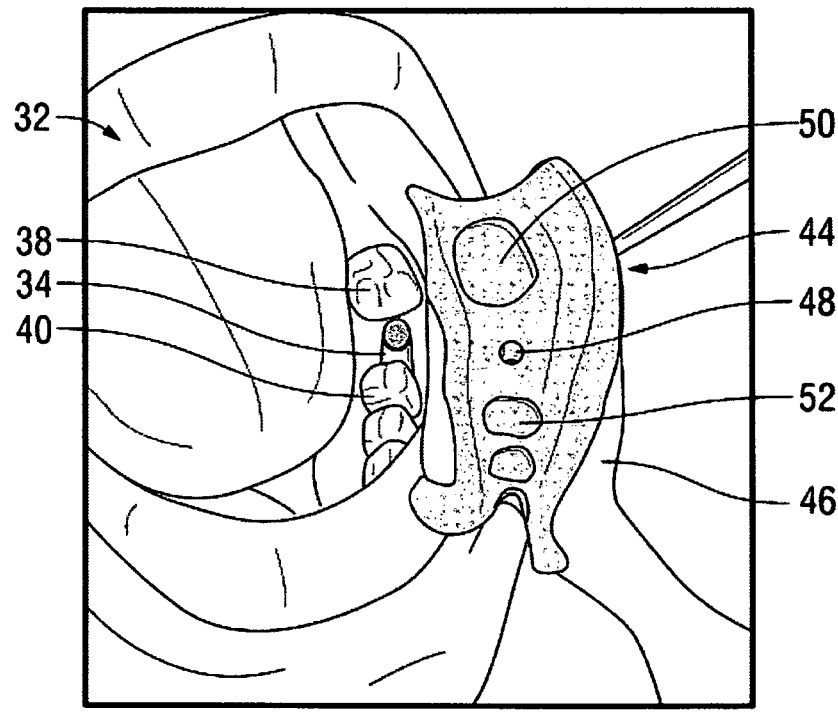
FIG. 4 depicts an impression obtained from the implant abutment of FIG. 2.

FIG. 4 depicts the mouth (32) of FIGS. 2 and 3, having the implant abutment (34) secured therein between adjacent teeth (38, 40), after an impression (44) of the implant abutment (34) and adjacent teeth (38, 40) has been obtained. The impression (44) can be acquired using any methods or equipment known in the art. FIG. 4 depicts an impression (44) that has been acquired through the provision of impression material, such as, polyvinyl siloxane, rubber base, dental alginate, silicone, polyether, hydrocolloid, or any similar material on to a bite tray (46) or a similar carrier, or into the mouth (32). Biting into the impression material creates the impression (44), which is shown having a first recessed region (48) formed by the implant abutment (34), a second recessed region (50) formed by the first adjacent tooth (38), and a third recessed region (52) formed by the second adjacent tooth (40). While conventional methods for providing a dental prosthesis often utilize an impression of all teeth within a patient's mouth, embodiments of the present method can be performed using an impression of only the implant abutment and a surrounding region of the mouth.

Returning to FIG. 1, after obtaining the impression (14), the depicted embodiment of the present method then includes removing the implant abutment from the mouth, securing the implant abutment to a second implant fixture external to the mouth, and placing the implant abutment within the corresponding location in the impression (16).

Figure 5:
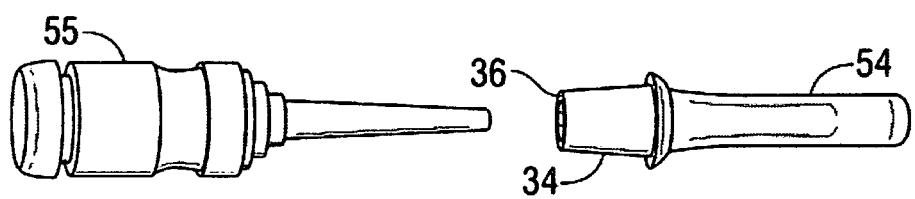
FIG. 5 depicts the implant abutment of FIG. 2 installed within an additional implant fixture.

FIG. 5 depicts the implant abutment (34) removed from the mouth (not shown in FIG. 5). The implant abutment (34) has been secured to an additional implant fixture (54) of similar or identical construction to the implant fixture implanted within the mouth intended to receive the implant abutment (34), using a securing tool (55), which is depicted as a specialized screwdriver designed for insertion into the opening (36) of the implant abutment (34) to thread a hex screw or similar threaded member (not visible in FIG. 5) into the additional implant fixture (54). After securing the implant abutment (34) to the additional implant fixture (54), the implant abutment (34) and additional implant fixture (54) can be placed within a corresponding location in the impression.

Figure 6:
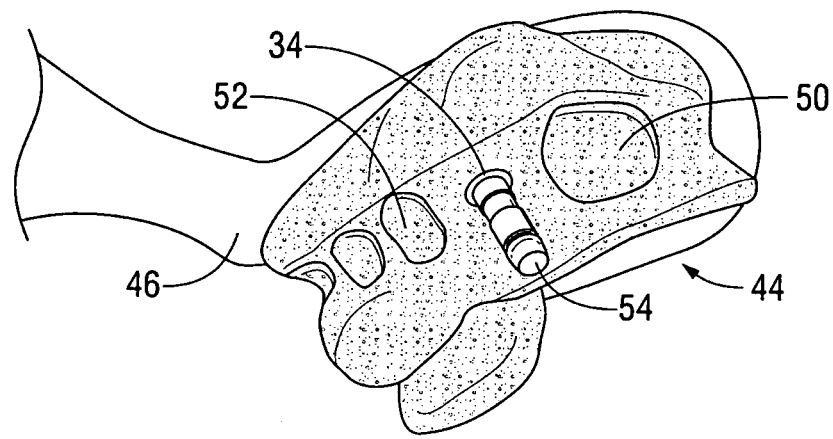
FIG. 6 depicts the implant abutment an additional implant fixture of FIG. 5 placed within a corresponding region of the impression of FIG. 4.

FIG. 6 depicts the impression (44) of FIG. 4 disposed on the bite tray (46), having the implant abutment (34) of FIG. 5 inserted into the first recessed region (not visible in FIG. 6), such that the additional implant fixture (54) protrudes from the impression adjacent the second and third recessed regions (50, 52).

Returning to FIG. 1, following transfer of the implant abutment to the impression, a mold material, such as bite set/record and/or gingival reproduction material, or any similar material that will harden and/or set, is provided into the impression and/or into a cavity of a transfer member (18) usable to form a mold of the impressed implant abutment and surrounding region of the mouth. Just before placing material into the impression record, a separating and/or lubricating agent can be sprayed into the impression to prevent the similar materials from adhering to one another while setting within the impression, to form the replica of the mouth. The second implant fixture is placed into the cavity while placing the impression over the mold (20), such that the mold material acquires the shape of the impression. After the mold material has hardened, the impression is removed from the transfer member while the mold and implant abutment are retained therein, such that the implant abutment can be modified while within the mold (22).

Figure 7A:
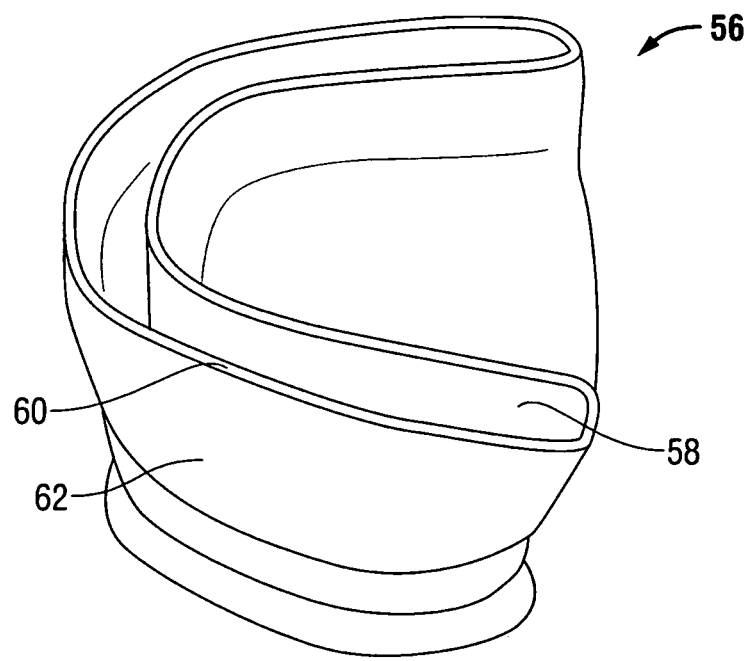
FIG. 7A a perspective view of a transfer member usable to receive the impression and implant fixture of FIG. 6 and form a corresponding mold.

Referring now to FIG. 7A, a top perspective view of an embodiment of a transfer member (56) usable with one or more embodiments of the present method is shown. The transfer member (56) includes a generally curved cavity (58) and/or well defined by a curved ridge (60), the cavity (58) having a curvature that approximates that of gingival tissue within the mouth and a depth sufficient to accommodate at least a portion of an implant fixture while an attached implant abutment protrudes from a mold within the cavity (58). In an embodiment of the invention, the cavity (58) can have a width at its base that is larger than the width at the top of the ridge (60) to facilitate retention of mold materials when materials are pulled from the transfer member (56). A base portion (62), usable as a handle, is disposed beneath the cavity (58). In an embodiment of the invention, the base portion (62) can include orifices or similar features useable to mount the transfer member (56) to an articulator or similar stand to enable a user to access and modify the contents of the cavity (58) without manually manipulating the transfer member (56). The transfer member (56) can be made from any generally rigid, solid material able to retain mold materials and withstand manual manipulation during the formation of molds and the modification of implants disposed within such molds. In an embodiment of the invention, the transfer member (56) can be formed from acrylic. In an alternate embodiment of the invention, the transfer member (56) can be formed from aluminum, or another similar metal or alloy.

Figure 7B:
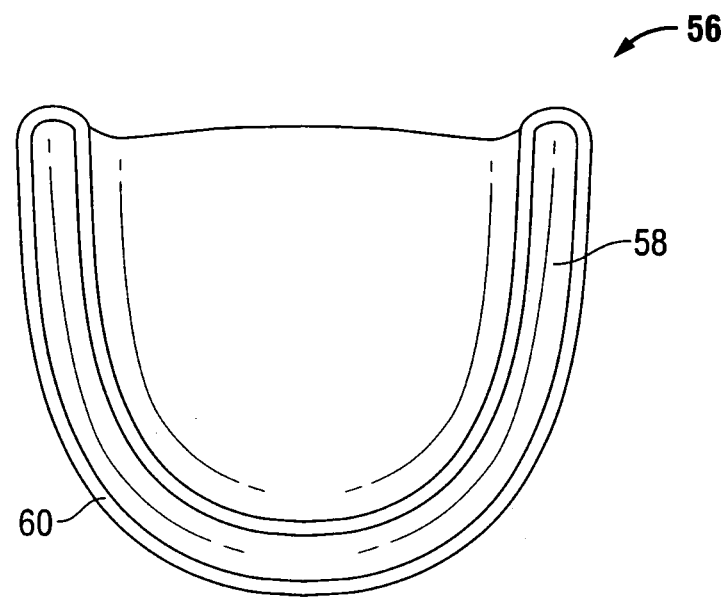
FIG. 7B depicts a top view of the transfer member of FIG. 7A.

FIG. 7B depicts a top view of the transfer member (56) of FIG. 7A, in which the cavity (58), defined by the ridge (60) is shown. The ridge (60) is depicted as a generally continuous shape having a front ridge disposed exterior to a back ridge.

Figure 7C:
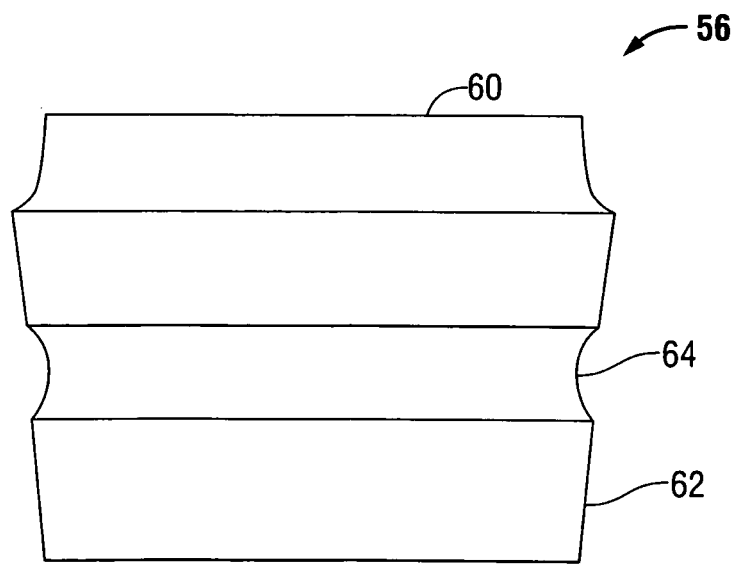
FIG. 7C depicts a front view of the transfer member of FIG. 7A.

FIG. 7C depicts a front view of the transfer member (56) of FIG. 7A. The ridge (60) is visible disposed above the base portion (62). The base portion (62) is depicted having a groove (64) disposed therein, usable to accommodate one or more fingers to facilitate manual gripping and manipulating of the transfer member (56). While FIG. 7C depicts only a single groove (64) along the base portion (62), it should be understood that any manner of grooves and/or gripping aids can be provided, or such elements can be omitted.

Figure 7D:
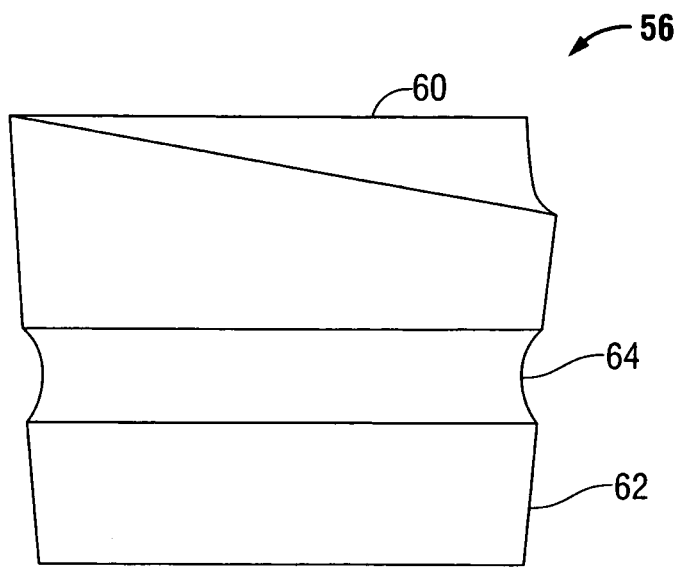
FIG. 7D depicts a side view of the transfer member of FIG. 7A.

FIG. 7D depicts a side view of the transfer member (56) of FIG. 7A, in which the ridge (60) is shown disposed above the base portion (62), the base portion (62) including a groove (64) for facilitating use of the base portion (62) as a handle.

Figure 7E:
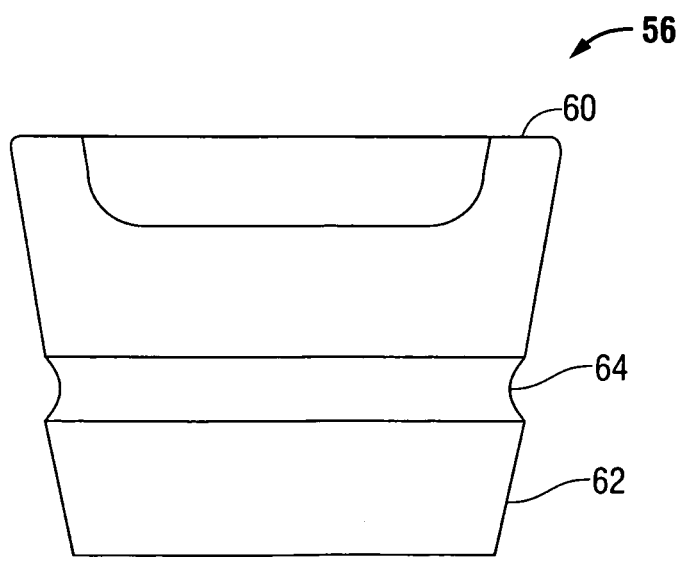
FIG. 7E depicts a back view of the transfer member of FIG. 7A.

FIG. 7E depicts a back view of the transfer member (56) of FIG. 7A, in which the ridge (60) is shown at the top of the transfer member (56), defining a cavity (not visible in FIG. 7E), above the base portion (62). The base portion is shown having a groove (64), as described previously.

Figure 8A:
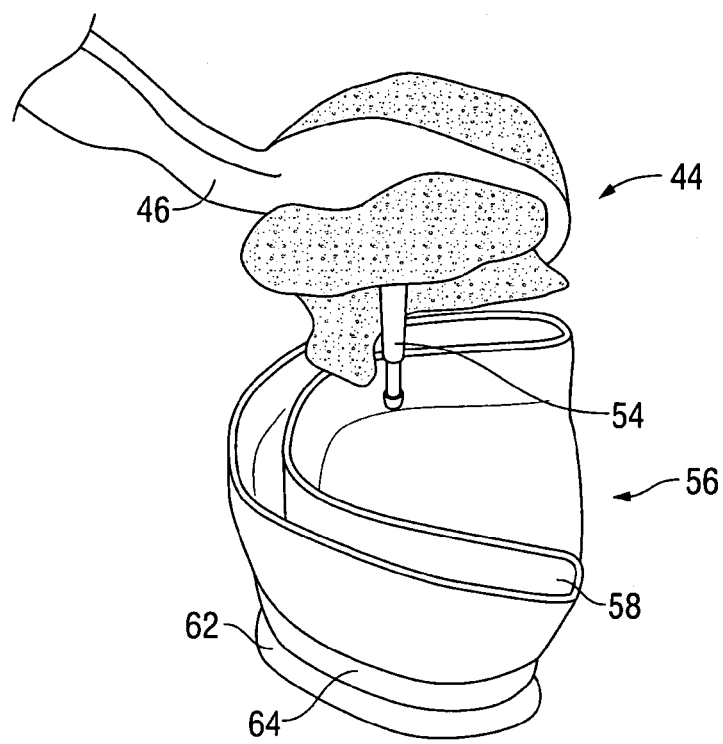
FIG. 8A depicts the transfer model of FIGS. 7A through 7E and the impression and implant fixture of FIG. 6 prior to formation of a mold.

FIG. 8A depicts the impression (44) of FIG. 4 disposed on the bite tray (46) with the additional implant fixture (54) protruding therefrom. The transfer member (56) of FIG. 7A is also shown, having the cavity (58) defined by the ridge (60) disposed above the base portion (62). After filling the cavity (58) and/or the impression (44) at least partially with a mold material, as described previously, the impression (44) can be placed over the cavity (58) such that the additional implant fixture (54) protrudes therein, permitting the implant fixture (54) to be retained in the mold formed by the mold material while the mold material acquires the shape of the impression (44).

Figure 8B:
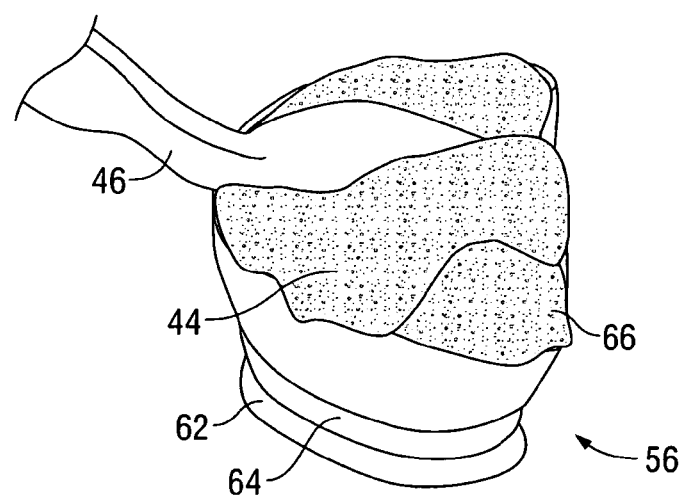
FIG. 8B depicts the transfer model and impression of FIG. 8A during the process of forming a mold.

FIG. 8B depicts the impression (44) disposed over the transfer member (56) after mold material (66) has been applied to the transfer member (56) and/or to the impression (44). Placement of the impression (44) over the mold material (66) causes the mold material (66) to acquire the shape of the recessions (not visible in FIG. 8B) within the impression (44). The additional implant fixture (not visible in FIG. 8B) of FIG. 8A is disposed within the cavity (not visible in FIG. 8B) of the transfer member (56), such that when the mold material (66) has hardened to form a mold, the impression (44) can be removed while the implant fixture is retained within the mold. The resulting mold will thereby have the shape of the recessions within the impression (44) that correspond to adjacent teeth, while the implant abutment (not visible in FIG. 8B) will protrude from the mold in a position corresponding to the position within the mouth in which the implant abutment will be installed.

Returning now to FIG. 1, after placing the second implant fixture into the cavity of the transfer member while placing the impression over the cavity to form the mold (20), and permitting the mold material to harden, the impression can be removed from the transfer member while the mold and implant abutment are retained, and the implant abutment can be subsequently modified (22), such as through grinding and/or machining as known in the art.

Figure 9A:
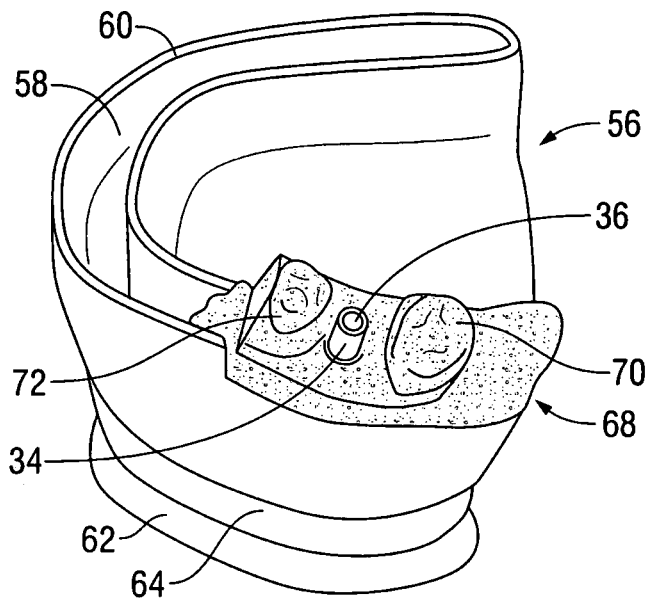
FIG. 9A depicts the mold formed during the process of FIG. 8B disposed within the transfer model.

FIG. 9A depicts a mold (68) of the portion of the mouth into which the implant abutment (34) will be installed, disposed within the cavity (58) of the transfer member (56), following removal of the impression. The mold (68) includes a first portion (70) formed from the recession of the impression created by the first adjacent tooth of FIG. 2, and a second portion (72) formed from the recession of the impression created by the second adjacent tooth of FIG. 2. The implant abutment (34) protrudes through the mold (68) in a position between the first and second portions (70, 72) corresponding to the position within the mouth into which the implant abutment (34) will be installed, while the implant fixture (not visible in FIG. 9A) extends within the mold (68) and into the cavity (58) of the transfer member (56). Use of the base portion (62) of the transfer member (56) as a handle enables manual modifications, such as grinding and/or machining, and other customizations, as known in the art, to be performed on the implant abutment (34) external to the mouth.

Figure 9B:
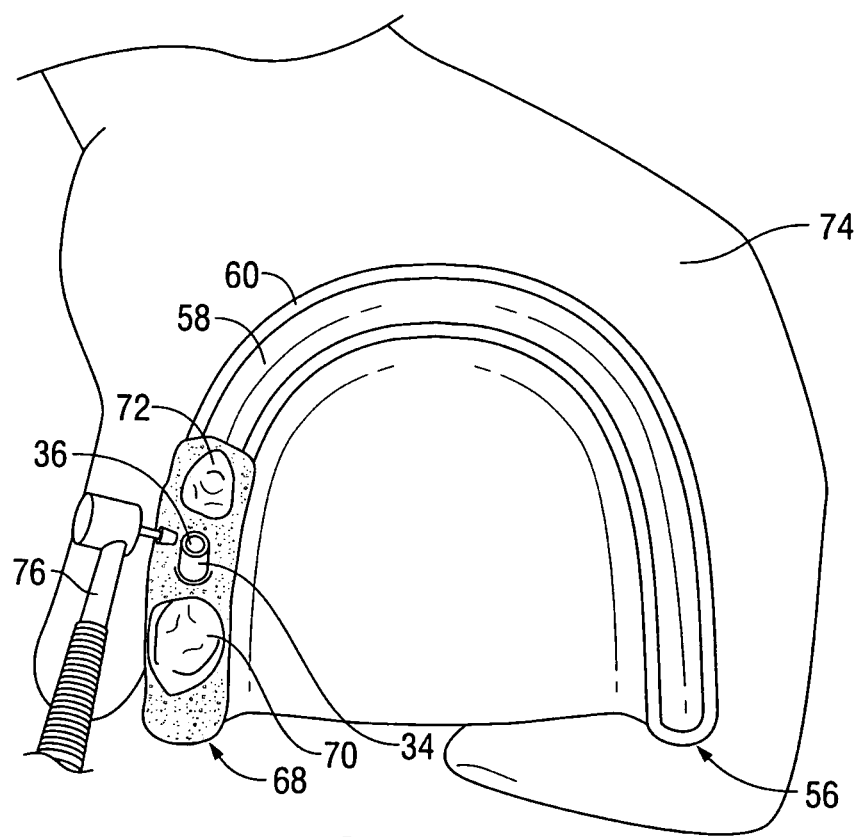
FIG. 9B depicts the mold and transfer model of FIG. 9A during the process of modifying the implant abutment.

FIG. 9B depicts an embodiment of the process of modifying and/or customizing the implant abutment (34), in which the transfer member (56) having the mold (68) disposed within the cavity (58) is shown being gripped and manually manipulated by a hand (74), facilitated by a groove (not visible in FIG. 9B) within the base portion (not visible in FIG. 9B). A grinding apparatus (76) is thereby usable to modify the implant abutment (34), using the first and second portions of the mold (70, 72) corresponding to adjacent teeth. Modification and/or customization of an implant abutment in this manner would be impossible within the mouth of a patient, while preparation of a replica mold and modification of an implant abutment would normally be performed using specialized equipment in a laboratory setting.

Figure 10:
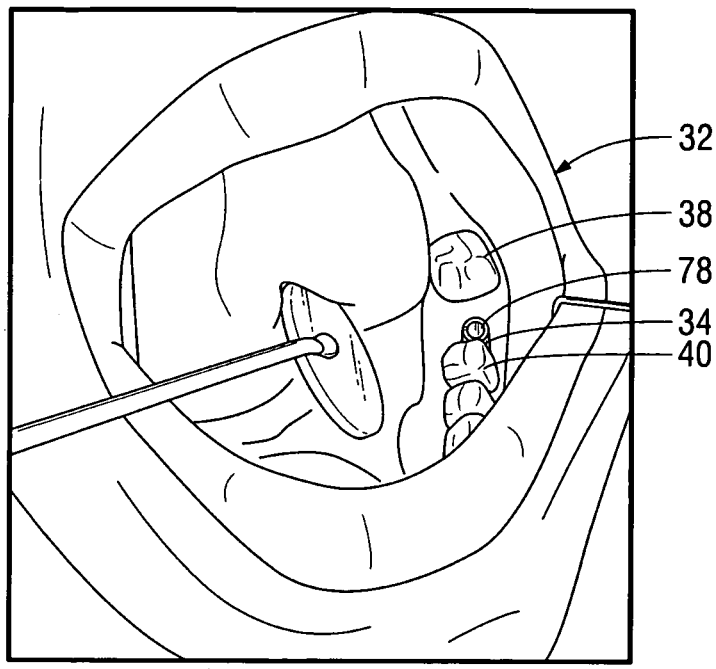
FIG. 10 depicts a modified implant abutment installed within a mouth.

Returning now to FIG. 1, after modifying and/or customizing the implant abutment as necessary, using the mold, the implant abutment can be removed from the mold, such as by breaking the mold or simply pulling the implant abutment and additional implant fixture therefrom, disconnected from the additional implant fixture, and returned to the implant fixture within the mouth (24). FIG. 10 depicts the mouth (32) of FIG. 2, having a modified implant abutment (78), having a bore (e.g., opening (36)) therethrough, installed between the first and second adjacent teeth (38, 40). While the specific modifications and/or customizations applied to an implant abutment can vary, FIG. 10 depicts the modified implant abutment (78) having a shorter height than the original implant abutment (34, depicted in FIG. 2).

Figure 11:
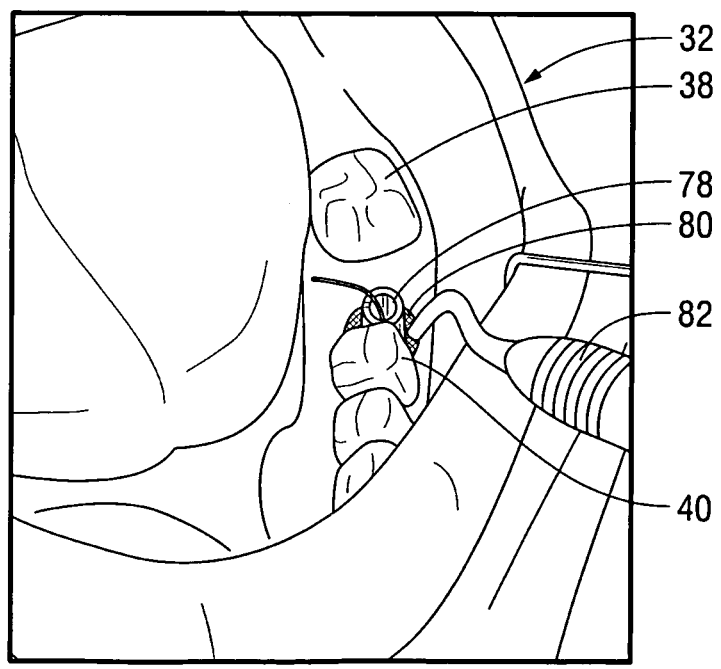
FIG. 11 depicts a gingival retraction cord being placed around the modified implant abutment of FIG. 10 to facilitate obtaining an impression thereof.

Returning to FIG. 1, a second impression of the modified implant abutment and a surrounding region of the mouth can then be obtained by blocking the access hole in the modified implant abutment (26), if necessary, then placing a length of cord around the modified implant abutment to retract adjacent gingival tissue therefrom (28). FIG. 11 depicts the mouth (32) of FIG. 10 having the modified implant abutment (78) installed therein between the first and second adjacent teeth (38, 40). A length of cord (80) is shown having been placed to retract surrounding gingival tissue from the modified implant abutment (78). Placement of the cord (80) in this manner facilitates obtaining an impression of the modified implant abutment (78) usable to fabricate and fit a crown or other prosthesis. FIG. 11 depicts the cord (80) being placed about the modified implant abutment (78) using a cord tucking apparatus (82) shaped to maximize contact with the cord (80) while minimizing contact with the modified implant abutment (78).

Use of gingival retraction cords to retract gingival tissue adjacent to dental implants can be facilitated through use of specialized dental apparatuses, which can be formed from titanium, plastic, or any other material that does not damage the implant body or abutment, to prevent scratching or damaging of the implant abutment, or otherwise causing discomfort to the patient. Conventional cord packing instruments generally include a narrow tip with a single point of contact that requires numerous strokes to forcibly pack a cord beneath a gum line. In an embodiment of the invention, a usable cord tucking instrument can include a concave region with an arcuate tip, the concave region having a radius of curvature relative to the base of the implant abutment such that in use, the arcuate tip contacts a length of the cord while minimizing contact between the cord tucking tool and the implant abutment. Numerous apparatuses and methods for placing a cord beneath a gum line adjacent to an implant abutment, usable within the scope of selected embodiments of the invention, are described in co-pending U.S. patent application Ser. No. 12/589,728, entitled "Gingival Cord Tucker for Use with Dental Implants," which is incorporated herein in its entirety by reference.

Figure 12:
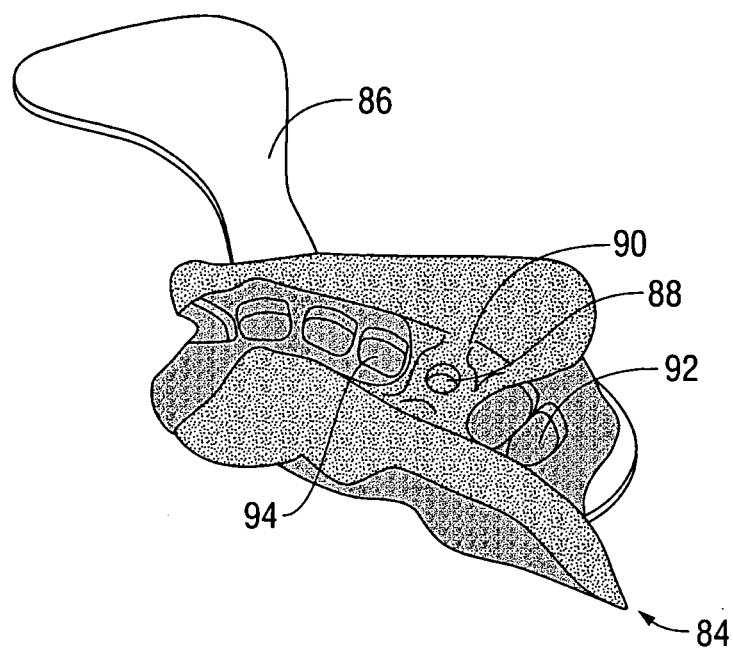
FIG. 12 depicts an impression obtained from the modified implant abutment of FIG. 11.

Returning to FIG. 1, following placement of the cord, the cord can then be removed, impression material can be applied to the modified implant abutment to create the second impression, and a temporary crown can be fabricated using the second impression (30). FIG. 12 depicts a second impression (84) disposed on a bite tray (86), formed through application of impression material around the modified implant abutment and the surrounding region of the mouth. The second impression (84) is shown having a region corresponding to the modified implant abutment (88), and a region corresponding to the cord (90) disposed between two regions corresponding to adjacent teeth within the mouth (92, 94).

Figure 13:
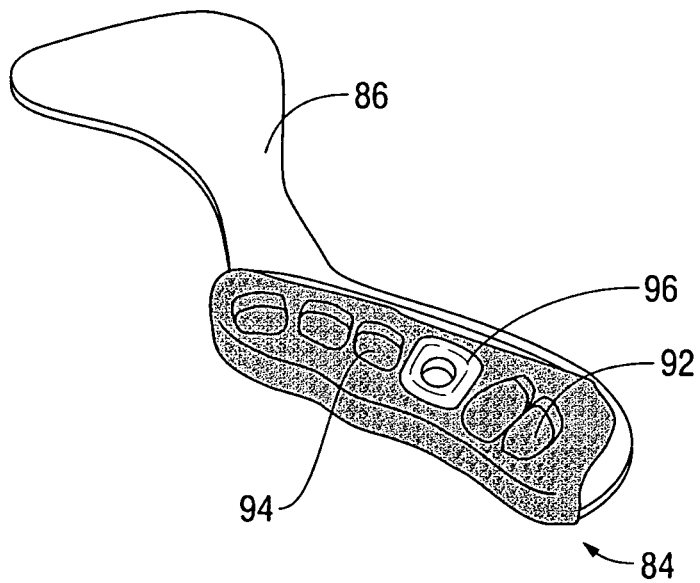
FIG. 13 depicts a temporary crown fabricated using the impression of FIG. 12 and disposed thereon.
Figure 14:
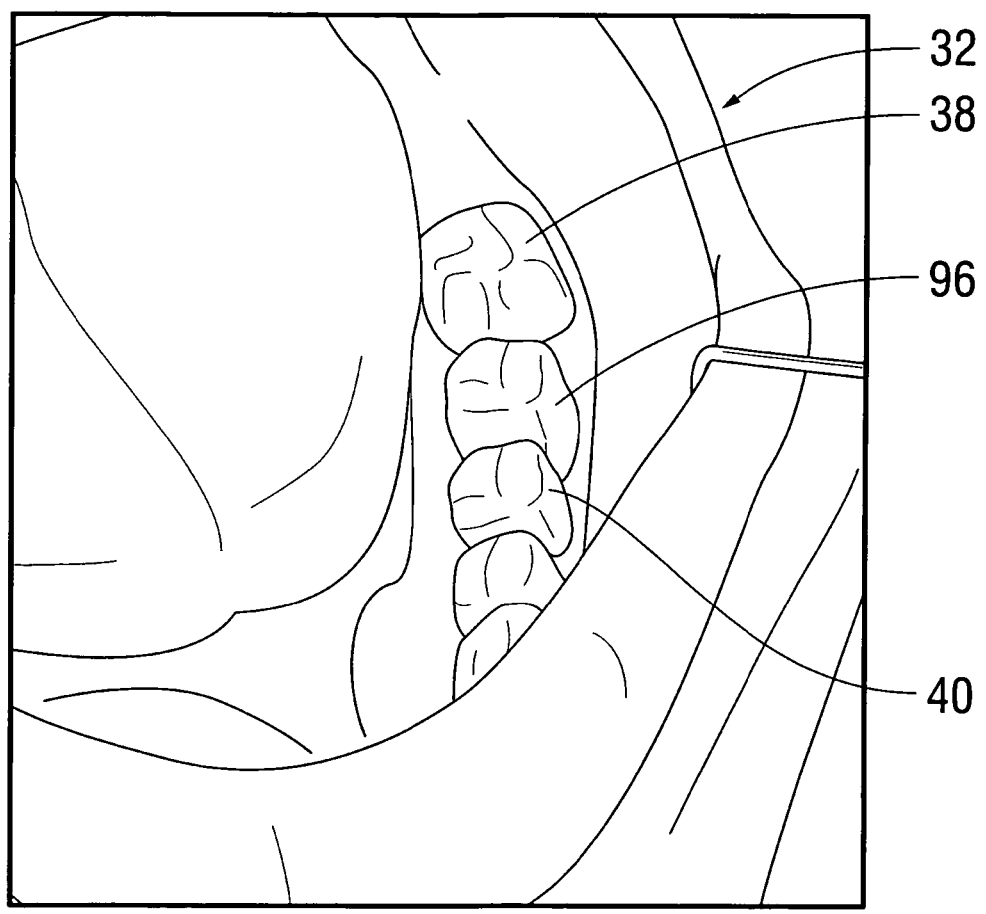
FIG. 14 depicts the temporary crown of FIG. 13 installed within the mouth of FIG. 10.

FIG. 13 depicts the second impression (84) over which a temporary crown (96) has been placed to occupy the regions corresponding to the modified implant abutment and the cord (88, 90). Using the regions that correspond to both the modified implant abutment and the cord (88, 90), and those corresponding to the adjacent teeth (92, 94), the temporary crown (96) can be appropriately sized, shaped, and fitted, such that the temporary crown (96) can be securely installed over the modified implant abutment within a patient's mouth. FIG. 14 depicts the temporary crown (96) installed within the mouth (32), between the first and second adjacent teeth (38, 40). The temporary crown (96) is disposed over the modified implant abutment (not visible in FIG. 14), after reinstallation of the modified implant abutment within the mouth (32). It should be understood that while FIGS. 13 and 14 depict preparation of a temporary crown for installation over the modified implant abutment, embodiments of the invention are usable to prepare any type of dental prosthesis for installation, including but not limited to bridges and permanent crowns.

Embodiments of the present invention thereby provide methods and apparatuses for providing a dental prosthesis to a patient that can be performed on-site, without requiring expensive and/or time-consuming laboratory procedures and multiple office visits by a patient. In an embodiment of the invention, a patient can be provided with a customized implant abutment and a temporary crown in a single office visit. Embodiments of the present invention also enable manual manipulation and customization of molds and implant abutments using equipment readily available on-site, at the dental office, including a transfer model and implant cord placing instruments for use in customizing the implant abutment and temporary crown or dental prostheses to the patient.

While the present invention has been described with emphasis on certain embodiments, it should be understood that within the scope of the appended claims, the present invention can be practiced other than as specifically described herein.

What is claimed is:

1. A method for providing a mouth with a dental prosthesis, the method comprising the steps of:
   securing an implant abutment to an implant fixture within a mouth, wherein the implant abutment comprises an opening adapted for facilitating engagement between the implant abutment and the implant fixture;
   blocking the opening in the implant abutment to prevent entry of impression material therein;
   obtaining an impression of the implant abutment and unblocking the opening, wherein the impression comprises a location corresponding to the implant abutment;
   removing the implant abutment from the mouth, securing the implant abutment to a second implant fixture external to the mouth, and placing the implant abutment in the location corresponding to the implant abutment in the impression such that the second implant fixture protrudes therefrom;
   placing mold material into the impression, a cavity of a transfer member, or combinations thereof;
   placing the second implant fixture into the cavity while placing the impression over the cavity to form a mold;
   removing the impression from the transfer member, wherein the mold, the second implant fixture, and the implant abutment attached thereto are retained within the mold such that the implant abutment protrudes therefrom;
   modifying the implant abutment while the implant abutment protrudes from the mold and is attached with the transfer member to form a modified implant abutment;
   disengaging the modified implant abutment from the second implant fixture and engaging the modified implant abutment to the implant fixture in the mouth;
   blocking the opening in the modified implant abutment to prevent entry of impression material therein;
   placing a gingival refraction cord around the implant abutment to retract gingival tissue therefrom;
   removing the gingival retraction cord and obtaining a second impression of the modified implant abutment;
   using the second impression to fabricate a temporary crown; and
   installing the temporary crown over the modified implant abutment.

2. The method of claim 1, wherein the step of securing the implant abutment to the implant fixture within a mouth, the step of securing the implant abutment to the second implant fixture external to the mouth, or combinations thereof, comprises threading the implant abutment using a screw.

3. The method of claim 1, wherein the step of obtaining an impression of the implant abutment further comprises obtaining an impression of at least one first tooth disposed on a first side of the implant abutment, and at least one second tooth disposed on a second side of the implant abutment, to facilitate modification of the implant abutment to correspond to said at least one first tooth and said at least one second tooth.

4. The method of claim 1, wherein the step of obtaining the second impression of the modified implant abutment comprises:
   providing impression material to the implant abutment such that the impression material flows between the implant abutment and the gingival tissue to form the impression.

5. The method of claim 1, wherein the step of placing a gingival retraction cord around the implant abutment comprises contacting the cord with a cord tucking tool comprising a concave region with an arcuate tip, wherein the concave region comprises a radius of curvature sized relative to the base of the implant abutment such that the arcuate tip contacts a length of the cord while minimizing contact between the cord tucking tool and the implant abutment.

6. The method of claim 1, wherein the transfer member comprises a curved cavity comprising a size and a shape corresponding to gingival tissue of the mouth, disposed above the handle portion.

7. The method of claim 6, wherein the curved cavity comprises a top having a first width and a bottom having a second width, wherein the first width is less than the second width.

8. The method of claim 6, where the curved cavity has a depth corresponding to a selected portion of the second implant fixture.

9. The method of claim 1, further comprising the step of applying a separating agent to the impression prior to providing the mold material to the impression for preventing the mold material from adhering to the impression.

10. The method of claim 1, wherein the step of obtaining the impression of the implant abutment comprises providing impression material to the implant abutment and a surrounding portion of the mouth such that the impression comprises a region corresponding to the implant abutment, and wherein the step of modifying the implant abutment comprises providing the implant abutment with a shape to accommodate the dental prosthesis within the surrounding portion of the mouth.

11. The method of claim 1, wherein the step of modifying the implant abutment comprises manually manipulating the transfer member containing the mold and the implant abutment using a handle.

12. The method of claim 1, wherein the transfer member comprises a curved cavity comprising a size and a shape corresponding to gingival tissue of the mouth, disposed above a handle portion.

13. The method of claim 12, wherein the curved cavity comprises a top having a first width and a bottom having a second width, wherein the first width is less than the second width.

14. The method of claim 1, wherein the method is performed within the span of a single patient visit.

* * * * *